(12) United States Patent
Jacob et al.

(10) Patent No.: US 7,547,433 B2
(45) Date of Patent: *Jun. 16, 2009

(54) LIQUID FORMULATIONS FOR THE PREVENTION AND TREATMENT OF MUCOSAL DISEASES AND DISORDERS

(75) Inventors: Jeremy E. Jacob, Lewisville, TX (US); David P. Nowotnik, Colleyville, TX (US); Christiane M. Baud, Dallas, TX (US)

(73) Assignee: Access Pharmaceuticals, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/077,459

(22) Filed: Feb. 15, 2002

(65) Prior Publication Data

US 2002/0168334 A1   Nov. 14, 2002

Related U.S. Application Data

(60) Provisional application No. 60/269,049, filed on Feb. 15, 2001.

(51) Int. Cl.
*A61K 8/00* (2006.01)
*A61K 8/18* (2006.01)
*A61K 47/32* (2006.01)
*A61Q 11/00* (2006.01)

(52) U.S. Cl. ............ 424/49; 424/401; 424/78.18; 424/78.24; 424/78.29; 424/78.31; 424/78.35; 514/772.1; 514/772.5; 514/772.7; 514/780; 514/781; 514/782; 514/901

(58) Field of Classification Search ............... 514/772, 514/772.1, 772.2, 772.3, 772.4, 772.5, 772.6, 514/772.7, 781, 901; 424/400, 484, 486, 424/487, 488
See application file for complete search history.

(56) References Cited

U.S. PATENT DOCUMENTS

| | | | |
|---|---|---|---|
| 4,615,697 A | | 10/1986 | Robinson |
| 4,738,842 A | | 4/1988 | Dow et al. |
| 4,851,393 A | * | 7/1989 | Rha et al. .................. 514/54 |
| 5,081,158 A | | 1/1992 | Pomerantz |
| 5,403,578 A | | 4/1995 | Gordon |
| 5,458,879 A | * | 10/1995 | Singh et al. .............. 424/400 |
| 5,462,749 A | | 10/1995 | Rencher |
| 5,474,768 A | | 12/1995 | Robinson |
| 5,543,150 A | | 8/1996 | Bologna et al. |
| 5,667,492 A | | 9/1997 | Bologna et al. |
| 5,900,230 A | | 5/1999 | Cutler |
| 5,968,500 A | | 10/1999 | Robinson |
| 5,989,535 A | * | 11/1999 | Nayak .................. 424/78.02 |
| 6,017,521 A | | 1/2000 | Robinson et al. |
| 6,056,950 A | * | 5/2000 | Saettone et al. ......... 424/78.04 |
| 6,071,959 A | | 6/2000 | Rhodes et al. |
| 6,103,266 A | | 8/2000 | Tapolsky et al. |
| 6,166,044 A | | 12/2000 | Sandborn et al. |
| 6,375,963 B1 | | 4/2002 | Repka et al. |
| 6,632,423 B2 | | 10/2003 | Jafari et al. |
| 2002/0076421 A1 | | 6/2002 | Dobrozsi |
| 2002/0103219 A1 | | 8/2002 | Jacob |
| 2002/0142042 A1 | * | 10/2002 | Mumper et al. ............ 424/487 |
| 2003/0060486 A1 | | 3/2003 | Jacob et al. |
| 2003/0098438 A1 | * | 5/2003 | Haslin ..................... 252/70 |
| 2005/0281862 A1 | * | 12/2005 | Karakelle et al. .......... 424/427 |

FOREIGN PATENT DOCUMENTS

| | | |
|---|---|---|
| EP | 07565664 A1 | 2/1997 |
| EP | 0765664 A | 4/1997 |
| EP | 0765664 A1 | 4/1997 |
| GB | 1593097 | 7/1981 |
| GB | 1593097 A | 7/1981 |
| NZ | 285761 | 5/1997 |
| NZ | 282537 | 9/1998 |
| US | 6071959 A | 6/2000 |
| US | 6103266 A | 8/2000 |
| US | 6166044 A | 12/2000 |
| WO | 96/09829 | 4/1996 |
| WO | 9609829 | 4/1996 |
| WO | 9609829 A | 4/1996 |
| WO | 9801112 | 1/1998 |
| WO | 9801112 A | 1/1998 |
| WO | 99/63986 | 12/1999 |
| WO | 9963986 A | 12/1999 |
| WO | 00/50078 | 8/2000 |
| WO | 0050078 | 8/2000 |
| WO | 02/09637 A2 | 2/2002 |
| WO | 0209637 A2 | 2/2002 |

OTHER PUBLICATIONS

DeCordi, D, Martina, S, "Gelclair: potentially an efficacious treat for chemotherapy-induced mucositis", 2001, 10-12.

Innocenti, M. Moscatelli, G, Lopez, S, "Efficacy of Gelclair in Reducing Pain in Patients with Oral Lesions-Preliminary Findings from an Open Pilot Study", 2001.

Berndtson, J., "A Preliminary Study of Orassist (Gelclair) in the management of Oral Mucositis", 2001, 17-21, Svensk Sjukhustandlak artidning.

(Continued)

*Primary Examiner*—Frederick Krass
*Assistant Examiner*—Benjamin Packard
(74) *Attorney, Agent, or Firm*—Antoinette F. Knoski, Esq.; Foley & Lardner LLP (57) ABSTRACT

Stable, viscous, mucoadhesive aqueous compositions which are useful for the prevention and treatment of ulcerative, inflammatory, and/or erosive disorders of mucous membranes and/or the delivery of pharmaceutically active compounds to mucosal surfaces for topical treatment or transfer to the systemic circulation.

18 Claims, 5 Drawing Sheets

OTHER PUBLICATIONS

Editio Cantor Verlag, "Rote Liste 2000", 1-5,7,9,12-16,18,19,21, Rote ListeService Aulendorf XP002203083.

Dr. Marcello Innocenti, Clinical Evaluation of Gelcair Concentrated Oral Gel, a new option for treating painful oral conditions, pp. 1-4, Milan, Italy, (2001).

PDR 21 Edition 2000, Physicians Desk Reference for Nonprescription Drugs and Dietary Supplements, pp. 640 and 787.

Dr. Heddie Sedano, Oral Complications During Cancer Treatment, Jun. 13, 2002, pp. 1-5.

Jelka Korbar-Smid et al, An Oxtetracycline Formulation to be Applied at the Oral Mucosa, Aug. 5, 1975, pp. 271-276, University of Ljubljana.

Dixon J, Search Conducted on Hyaluronic Acid and Mucositis, May 29, 2002, pp. all, US.

Kaken Seiyaku KK, Abstract, JP 59186913, Apr. 4, 1983.

Tsumura & Co, Abstract JP 8291083, Apr. 17, 1995.

Cheng, K.K.F. et al. "Evaluation of an oral care protocol intervention in the prevention of chemotherapy-induced oral mucositis in paediatric cancer patients" *Eur. J. Cancer* (Nov. 2001) 37(16):2056-63.

Demarosi, F. et al. "Prevention and Treatment of Chemo- and Radiotherapy-Induced Oral Mucosistis" *Minerva Stomatol.* (May, 2002) 51(5):173-186.

Dodd, M.J. et al. "Risk Factors for Chemotherapy-Induced Oral Mucositis: Dental Appliances, Oral Hygiene, Previous Oral Lesions, and History of Smoking" *Cancer Invest.* (1999) 17(4):278-284.

Epstein, J.B. and A.W. Chow "Oral Complications Associated with Immunosuppression and Cancer Therapies" *Infectious Disease Clinics of North America* (Dec. 1999) 13(4):901-923.

Fulton, J.S. et al. "Management of Oral Complications" *Semin. Oncol. Nurs.* (Feb. 2002) 18(1):28-35.

Ghate, J.V. and J.L. Jorizzo "Behçet's Disease and Complex Aphthosis" *J. Am. Acad. Dermatol.* (Jan. 1999) 40(1):1-18.

Miles, D.A. and M.M. Howard "Disorders Affecting the Oral Cavity: Diagnosis and Management of Oral Lichen Planus" *Dermatologic Clinics* (Apr. 1996) 14(2):281-290.

Morales, A. et al. "Treatment of Refractory Interstitial Cystitis" *Int. Urogynecol. J.* (1996) 7(4):215-220.

Plevová, P. "Prevention and treatment of chemotherapy- and radiotherapy-induced oral mucositis: a review" *Oral Oncology* (Sept. 1999) 35:453-470.

Popovsky, J.L. and C. Camisa "New and Emerging Therapies for Diseases of the Oral Cavity" *Dermatologic Clinics* (Jan. 2000) 18(1):113-125.

Sonis, S.T. et al. "Validation of a New Scoring System for the Assessment of Clinical Trial Research of Oral Mucositis Induced by Radiation or Chemotherapy" *Cancer* (May 15, 1999) 85(10):2103-2113.

Sonis, S.T. et al. "Oral Complications of Cancer Therapy" *Oncology* (May 2002) 16(5):680-686, 691-692, 695.

Worthington, H.V. et al. "Interventions for treating oral mucositis for patients with cancer receiving treatment" *Cochrane Database Syst. Rev.* (2002) 1:CD001973, located at http://web19.epnet.com/citation.asp?rds=1&sxp=32&...%5B0+%2Dproximity+op.

International Search Report for PCT/US02/04577 dated Jun. 21, 2002.

Written Opinion for PCT/US02/04577 dated Sep. 16, 2003.

International Preliminary Examination Report for PCT/US02/04577 dated Jan. 12, 2004.

Buhse et al. (2005) "Topical drug classification," *International Journal of Pharmaceutics* 295:101-112.

Khandwala et al. (1997) "5% Amlexanox oral paste, a new treatment for recurrent minor aphthous ulcers: I. Clinical demonstration of acceleration of healing and resolution of pain," *Oral Surg Oral Med Oral Pathol Oral Radiol Endod* 83(2):222-230.

Rote Liste Service (Editor), "Rote Liste 2000", Edition Cantor Verlag, Aulendorf XP002203083.

Loher, F., International Search Report, dated Jun. 21, 2002, Europe.

\* cited by examiner

LIQUID FORMULATIONS FOR THE PREVENTION AND TREATMENT OF MUCOSAL DISEASES AND DISORDERS

FIELD OF THE INVENTION

The present invention relates to compositions and methods of manufacture of stable, viscous, mucoadhesive liquid formulations, and the use of these compositions to coat mucocutaneous surfaces, such as those in the oral cavity, the nasal cavity, the gastrointestinal and respiratory tracts, the vagina, and the bladder, etc. to prevent and/or treat mucosal diseases and disorders, including those which are ulcerative, inflammatory, and/or erosive. The liquid dosage forms are sufficiently mobile to coat a wide area of the mucosal surface, but are also mucoadhesive and viscous to provide prolonged retention on the surface of the mucosa. The liquid compositions may be used without a known pharmaceutically active compound. One or more pharmaceutically active compounds may be included in the formulation to provide additional benefit in the topical treatment of diseases and disorders of the mucosa, or for drug delivery through the mucosa to the systemic circulation.

BACKGROUND INFORMATION

Mucous membranes provide a protective layer on the surface of several body cavities, such as the oral cavity, the nasal cavity, the gastrointestinal and respiratory tracts, the vagina, and the bladder. Cells within or glands adjacent to these membranes secrete mucus, a fluid or gel primarily composed of water, lipids, inorganic salts and mucin glycoproteins, which serve to form a protective barrier to inhibit passage of harmful materials to the underlying tissue. There are several diseases and disorders of these mucosal surfaces which can result in severe pain, irritation, erythema, and/or ulceration. Examples of such diseases in the oral cavity include aphthous ulcers, bullous pemphigoid, oral lichen planus, and oral mucous membrane contact dermatitis; examples of diseases of the nasal mucous membrane include sinusitis and rhinitis; an example for the bladder is interstitial cystitis. Certain diseases such as Behçet syndrome, can affect the mucocutaneous membranes of several regions of the body. Many other ulcerative mucocutaneous diseases are known. There are also painful ulcerative disorders of mucosal surfaces which result as an adverse side-effect in certain therapies, such as chemotherapy and radiation therapy. Examples of such side-effects include mucositis, esophagitis, and radiation proctitis.

The following section provides a brief description of these conditions

Aphthous Ulcers

Aphthous ulcers (also known as aphthous stomatitis and canker stores) are benign open sores in the mouth, which appears as a painful white or yellow sore (ulcer) surrounded by a bright red area. Aphthous ulcers can be categorized into three groups:

minor aphthous ulcers, the most common type, which recur in crops of 1 to 5 lesions, are less than 1 cm in diameter each, and usually affect the lips, buccal mucosa, mucobuccal and mucolabial sulci, and tongue;

major aphthous ulcers, which are greater than 2 cm in diameter, begin as solitary nodules, and subsequently destroy deeper tissue, resulting in scarring that affects the movable oral mucosa and posterior mucosal surfaces; and herpetiform ulcers, which are recurrent, multiple (10 to 100), shallow, pinpoint lesions 1 to 2 mm in diameter that may affect any part of the mucosa. The cause for any of the three types is not known, although autoimmune mechanisms are suspected.

The cause is unknown. There may be an inherited predisposition to their development. There may also be an immune system link. Ulcers may develop in response to mouth injury such as dental procedures or aggressive tooth cleaning. They may occur at the site of a bite when the tongue or cheek is bitten. They can also triggered by stress, dietary deficiencies (especially iron, folic acid, or vitamin B12), menstrual periods, hormonal changes, food allergies, and similar situations. They may occur with no identifiable cause. Canker sores usually appear on nonkeratinized mouth tissue including the inner surface of the cheeks and lips, tongue, soft palate, and the base of the gums. They usually begin with a tingling or burning sensation, followed by a red spot or bump that ulcerates. Pain spontaneously decreases in 7 to 10 days, with complete healing in 1 to 3 weeks. Occasionally, a severe occurrence may be accompanied by nonspecific symptoms of illness such as fever or malaise. Recurrence is common and may continue for years (sources: WebMD, Rakel: Conn's Current Therapy 2000, 52nd ed).

Aphthous ulcers are occasionally associated with macrocytic anemias or gluten-sensitive enteropathy and may become more frequent and severe in association with human immunodeficiency virus (HIV) infection (source: Goldman: Cecil Textbook of Medicine, 21st Ed.)

Behçet Syndrome

Behcet's disease is a chronic multisystem disease characterized by oral and genital aphthae, arthritis, cutaneous lesions, and ocular, gastrointestinal, and neurologic manifestations. It was first described by the Turkish dermatologist Hulusi Behcet in 1937 as "recurrent oral aphthous ulcers, genital ulcers, and 'hypopyon-uveitis.'" The diagnosis of Behcet's disease is based on clinical criteria as established by O'Duffy and Goldstein and the International Study Group. Complex aphthosis is the presence of almost constant, multiple oral or oral and genital aphthae in the absence of systemic manifestations. These patients must be distinguished from those with Behcet's disease.

The prevalence of Behcet's disease is higher in the Middle East and Japan where it is approximately 1 in 1000. The disease is far less common in northern Europe, the United States, and the United Kingdom. The mean age of onset ranges from the mid to late 20s to the fourth decade, according to several series, with a slightly higher male to female ratio. It is relatively rare in children and the elderly. Behcet's disease is also uncommon among black Africans who, when they are affected, tend to have more mucocutaneous features. Although a definitive pattern of inheritance has not been elucidated, familial cases have been reported. Patients with complex aphthosis are probably a subset of patients with recurrent aphthous stomatitis, which is defined as the recurrence of 1 or more painful oral ulcers at intervals ranging from days to months. The prevalence of recurrent aphthosis ranges from 5% to 66%. Onset may occur in childhood or adolescence and some patients experience a decrease in frequency with advancing age. (source: J. V Ghate and J. L. Jorizzo, "Behcet's disease and complex aphthosis", Journal of the American Academy of Dermatology, 1999, 40(1), 1-18.)

Bullous Pemphigoid

Bullous pemphigoid (BP) is an autoimmune, subepidermal blistering disease. The antigenic targets are components of the hemidesmosome; the 230-kD bullous pemphigoid antigen 1 and the 180-kD bullous pemphigoid antigen 2. It commonly affects patients in their seventh decade. About 40% of patients will experience oral involvement during the course of their disease.

The mainstay of treatment for BP is systemic corticosteroids. Bullous pemphigoid is usually exquisitely sensitive to these drugs, but significant side effects in a predominantly elderly patient population limits their long-term use at therapeutic doses. Steroid-sparing agents, such as dapsone, methotrexate, and azathioprine, have been used successfully. In addition, tetracycline and niacinamide have been shown to be effective, and this combination is frequently tried first to avoid toxicity from other drugs. (source: J. L. Popovsky and C. Camisa, "New and emerging therapies for diseases of the oral cavity", Dermatologic Clinics, 2000, 18(1), 113-125.).

Chemical and Radiation Cystitis

The term 'cystitis' covers a range of disorders commonly known "painful bladder" disease in which sufferers bladder and/or pelvic pain and irritative voiding symptoms (urgency, frequency, nocturia, dysuria). There are a variety of known causes, which includes the damaging side-effects of radiation therapy to the lower abdomen, and cytotoxic agents and/or their metabolites as they pass through the bladder following renal clearance.

Cyclophosphamide (Cytoxan), the most commonly used oxazaphosphorine, is an alkylating agent first used in the treatment of malignant tumors in Europe in 1957. Cyclophosphamide still has a role in the treatment of solid tumors and lymphomas, as well as benign inflammatory states, Wegener's granulomatosis and rheumatoid arthritis being the most common. Other oxazaphosphorines—ifosfamide, trofosphamide, and sufosfamide—have been used since the 1970s for the treatment of solid malignancies and lymphomas. Dose-limiting toxicity with these compounds is usually urinary tract toxicity.

Subsequent to treatment with these compounds, urinary symptoms including frequency, urgency, dysuria, and nocturia develop in as many as 24% of patients treated with oral Cytoxan.

Bladder pathology has been attributed to toxic metabolites of these compounds. Cyclophosphamide is broken down by hepatic microsomal cells to hydroxycyclophosphamide; then by target cells to aldophosphamide; and then to phosphoramide mustard, the active antineoplastic metabolite, and acrolein, which has no significant antitumor activity. Similarly, ifosfamide is metabolized to iphosphoramide mustard and acrolein. Urinary excretion of acrolein is believed to be the major source of urothelial toxicity. Most normal cells are able to break down the toxic metabolites and diminish their effect. Glutathione is a naturally occurring thiol that can confer such protection in most cells, but is present in low levels in urine.

Oxazaphosphorine toxicity has been demonstrated in several animal models with their systemic administration and by instillation of their normal metabolic products directly into the bladder. Urine from animals given these agents, when placed in other animal bladders, will reproduce these findings, while instillation of cyclophosphamide will not. Electron microscopy suggests the initial toxic effect is disruption of the plasma membrane and cytoplasmic matrix.

Bladder damage from these compounds is cumulative, and is generally dose related. "Cyclophosphamide cystitis" occurs frequently and early following intravenous (IV) therapy, especially dose-intensive regimens. Cystitis usually takes weeks to develop after oral treatment, but has been seen after as little as one dose. Fibrosis has been found in as many as 25% of children receiving high-dose cyclophosphamide. Severe hematuria and telangiectasia are more common in these patients. Oxazaphosphorine cystitis is potentiated by prior pelvic radiation.

Cystoscopy may reveal a tumor or changes compatible with cyclophosphamide cystitis. Acutely diffuse inflammation is seen. Chronic changes include a pale bladder mucosa with telangiectasia. Areas of edema can be present with patchy hemorrhagic areas that stain with methylene blue, an indicator of mucosal injury. Biopsies reveal hyperemia, hemorrhage, edema, mucosal thinning, and ulceration of the urothelium. Necrosis of mucosa, muscle, and small arterioles and telangiectasia can be present. Atypia can be prominent, and abundant mitoses often occur. These findings are similar to those seen after radiation therapy.(source: DeVita: Cancer: Principles and Practice of Oncology, 5th ed., Copyright© 1997 Lippincott-Raven Publishers).

Erythema Multiforme

Erythema multiforme often affects the oral cavity and is frequently recurrent. The classic cutaneous findings are targetoid lesions symmetrically distributed over the trunk and extremities. Studies show that as many as 70% of patients develop oral lesions, which are extremely painful and often debilitating. In more than 60% of patients, the attacks followed an episode of herpes simplex virus (HSV) infection. Acyclovir or one of the newer antiviral agents can be used to suppress recurrent HSV outbreaks and to prevent recurrent erythema multiforme. The current recommendations for daily suppression of HSV are acyclovir (400 mg twice daily), famciclovir (250 mg twice daily), or alacyclovir (500 mg daily). Suppressive doses are to be used for patients who experience more than six episodes a year of HSV or HSV-induced erythema multiforme.

Azathioprine (Imuran) can also be used to treat erythema multiforme. It should be used for patients who have severe mucosal involvement or in whom lesions continue to occur despite HSV suppression. In one study, 11 patients with severe disease failed to respond to acyclovir, dapsone, or antimalarials, but all cleared with azathioprine, 100 to 150 mg daily. Response was dose-dependent, and the condition relapsed when therapy was discontinued. Thalidomide has also been shown to be effective for recurrent erythema multiforme. (source: J. L. Popovsky and C. Camisa, "New and emerging therapies for diseases of the oral cavity", Dermatologic Clinics, 2000, 18(1), 113-125.)

Esophagitis

Esophagitis is a side-effect of the radiation therapy of the chest when the esophagus receives an unavoidable significant radiation dose.

Acute side effects occurring during the course of radiotherapy are organ specific and related to the fractionation scheme, total dose, and use of sequential or concomitant chemotherapy or radiosensitizers. They typically manifest in the second to third week of treatment. A significant concern of combined therapy is the increased toxicity, which may potentially outweigh the benefit from both modalities.

Most patients do not develop symptoms related to lung irradiation until the end of treatment. Some patients complain of a dry, nonproductive cough secondary to radiation effect on the trachea or bronchi. This reaction can last for several weeks after the completion of treatment. Radiation may also induce acute esophagitis during the course of therapy, which typically occurs during the second through fourth weeks of treatment, as well as shortly after completion. Chemotherapy and radiosensitizers appear to accelerate the onset and severity of symptoms. Agents such as 5-fluorouracil, doxorubicin, cisplatin, and mitomycin enhance the effect of radiation with regard to the esophagus. In general, acute esophagitis resolves shortly after the completion of radiotherapy, with few patients progressing to chronic esophagitis. Esophagitis presents with mild to severe swallowing difficulty requiring diet modification and nonnarcotic or narcotic analgesics, depending on severity. (source: DeVita: Cancer: Principles and Practice of Oncology, 5th ed)

Interstitial Cystitis

Interstitial cystitis (IC) has only recently been recognized as a major health problem. It encompasses a major portion of the "painful bladder" disease complex, which includes a large group of urologic patients with bladder and/or pelvic pain, irritative voiding symptoms (urgency, frequency, nocturia, dysuria), and negative urine cultures. Painful bladder diseases with a well-known cause include radiation cystitis, cyclophosphamide cystitis, cystitis caused by microorganisms that are not detected by routine culture methodology, and systemic diseases affecting the bladder.

One problem with defining IC is that the symptoms are in reality an exaggeration of normal sensations. Urinary frequency patterns can be related to fluid intake and age, and the signal or urge to void is considered an unpleasant or painful sensation by most persons. With no pathognomonic findings on pathologic examination, IC is truly a diagnosis of exclusion. It may have multiple causes and represent a final common reaction of the bladder to different types of insult. Thus, issues of definition are critical. To understand the current way IC is defined and how this came to be, a look back in time is helpful.

In 1987 there were 43,500 (perhaps up to 90,000) diagnosed cases of IC in the United States, approximately twice the prevalence in Finland found by Oravisto 12 years earlier. More interesting, women who were diagnosed by sampled urologists as actually having IC represented only 20% of the cases presenting with symptoms (chronic painful bladder, sterile urine) that were suggestive of this disease. On the basis of these data, from 250,000 to almost 500,000 patients in the United States might have had IC in 1987, depending on the assumptions used.

The median age of onset is 40 years.

Up to 50% of patients experience spontaneous remissions probably unrelated to treatment with a duration ranging from 1 to 80 months (mean 8 months).

Patients with IC are 10 to 12 times more likely than controls to report childhood bladder problems.

The time from symptom onset to diagnosis varied from 24 months for the patients most recently diagnosed to 51 months for members of the Interstitial Cystitis Association.

Taking the prevalence figure of 44,000, the IC-related incremental medical care cost in the United States was $116.6 million in 1987 and IC-related lost economic production was $311.7 million.

Intravesical lavage with one of a variety of preparations remains the standard treatment against which other treatments must be measured. A mainstay of the treatment of IC is the intravesical instillation of DMSO. DMSO is a product of the wood pulp industry and a derivative of lignin. It has exceptional solvent properties and is freely miscible with water, lipids, and organic agents. Pharnacologic properties include membrane penetration, enhanced drug absorption, anti-inflammatory properties, analgesic properties, collagen dissolution, muscle relaxation, and mast cell histamine release. In vitro effects on bladder function belie its positive effects in vivo. (source: Walsh: Campbell's Urology, 7th ed., Copyright© 1998 W. B. Saunders Company).

Mucositis

Oral mucositis is a significant problem in patients receiving chemotherapy or radiation therapy. Estimates of oral mucositis in cancer therapy range from 40% of those receiving standard chemotherapy to 76% of bone marrow transplant patients. Virtually all patients who receive radiation therapy to the head and neck area develop oral complications. Mucositis is not only painful, but it also can limit adequate nutritional intake and decrease the willingness of patients to continue treatment. More severe mucositis with extensive ulceration may require costly hospitalizations with parenteral nutrition and narcotics. Mucositis diminishes the quality of life and may result in serious clinical complications. A healthy oral mucosa serves to clear microorganisms and provides a chemical barrier that limits penetration of many compounds into the epithelium. A mucosal surface that is damaged increases the risk of a secondary infection and may even prove to be a nidus for systemic infection. Mucositis may result in the need to reduce dosage in subsequent chemotherapy cycles or to delay radiation therapy, which may ultimately affect patient response to therapy.

Normally, cells of the mouth undergo rapid renewal over a 7- to 14-day cycle. Both chemotherapy and radiation therapy interfere with cellular mitosis and reduce the ability of the oral mucosa to regenerate. Cancer chemotherapeutic drugs that produce direct stomatotoxicity include the alkylating agents, antimetabolites, natural products, and other synthetic agents such as hydroxyurea and procarbazine hydrochloride. Typical sequelae of these cytotoxic agents include epithelial hyperplasia, collagen and glandular degeneration, and epithelial dysplasia. Mucositis is an inevitable side effect of radiation. The severity of the mucositis is dependent on the type of ionizing radiation, the volume of irradiated tissue, the dose per day, and the cumulative dose. As the mucositis becomes more severe, pseudomembranes and ulcerations develop. Poor nutritional status further interferes with mucosal regeneration by decreasing cellular migration and renewal.

Direct stomatotoxicity is usually seen 5 to 7 days after the administration of chemotherapy or radiation therapy. In the nonmyelosuppressed patient, oral lesions heal within 2 to 3 weeks. The nonkeratinized mucosa is most affected. The most common sites include the labial, buccal, and soft palate mucosa, as well as the floor of the mouth and the ventral surface of the tongue. Clinically, mucositis presents with multiple complex symptoms. It begins with asymptomatic redness and erythema and progresses through solitary white elevated desquamative patches that are slightly painful to contact pressure. Following this large, acutely painful contiguous pseudomembranous lesions will develop with associated dysphagia and decreased oral intake. Histopathologically, edema of the retepegs is noted, along with vascular changes that demonstrate a thickening of the tunica intima with concomitant reduction in the size of the lumen and destruction of the elastic and muscle fibers of the vessel walls. The loss of the epithelial cells to the basement membrane exposes the underlying connective tissue stroma with its associated innervation, which, as the mucosal lesions enlarge, contributes to increasing pain. Oral infections, which may be due to bacteria, viruses, or fungal organisms, can further exacerbate the mucositis as well as lead to systemic infections. If the patient develops both severe mucositis and thrombocytopenia, oral bleeding may occur that is very difficult to treat.

A mucositis grading system gives the physician the ability to assess the severity of the mucositis in terms of both the pain and the patient's ability to maintain adequate nutrition so that a treatment plan can be appropriately constructed. There are many different grading systems; most are based on two or more clinical parameters, including erythema, pain, and problems with eating. An example of a common grading system is that proposed by the National Cancer Institute, which uses a numbering scale of 0 to 4. Grade 0 means no mucositis; grade 1, the patient has painless ulcers, erythema, or mild soreness; grade 2, the patient has painful erythema, edema, or ulcers but can eat; grade 3, the patient has painful erythema, edema, or ulcers and cannot eat; and grade 4, the patient requires parenteral or enteral support.

A standardized approach for the prevention and treatment of chemotherapy- and radiation-induced mucositis is essential; unfortunately, the efficacy and safety of most of the regimens have not been established. The prophylactic measures usually employed for the prevention of mucositis include chlorhexidine gluconate (Peridex), saline rinses, sodium bicarbonate rinses, acyclovir, amphotericin, and ice. Regimens commonly used for the treatment of mucositis and its associated pain include a local anesthetic such as lidocaine or Dyclone, Maalox or Mylanta, diphenhydramine (Benadryl), nystatin, or sucralfate. These agents are either used alone or in different combinations of the above medications made into a mouthwash. Other agents used less commonly include Kaopectate, allopurinol, vitamin E, beta-carotene, Kamillosan liquid, aspirin, antiprostaglandins, prostaglandins, MGI 209 (marketed as Oratect Gel), silver nitrate, and antibiotics. Oral and sometimes parenteral narcotics are used for pain relief. A new method utilizing capsaicin is currently under study to help relieve the pain. (source: DeVita: Cancer: Principles and Practice of Oncology, 5th ed., Copyright© 1997 Lippincott-Raven Publishers).

Oral Lichen Planus

Lichen planus (LP) is a common, idiopathic skin disorder affecting approximately 2% of the adult US population. Although its behavior on the skin is predictable and manageable using topical corticosteroids, oral lichen planus (OLP) has a more variable clinical course and is less responsive to topical corticosteroid therapy. There are multiple clinical presentations of OLP, and the disorders in some of these clinical forms can mimic many other types of oral lesions. Furthermore, some authors believe that certain clinical types of OLP may have a premalignant nature. Various drugs, topical and systemic, have been shown to induce lichenoid lesions through antigenic mechanisms.

There is even good evidence emerging that amalgam and dental plaque can act as antigens to induce OLP in some patients. The plaque form of OLP is seen more often in smokers. Women appear to be affected more often than men. Not all persons who develop skin lesions develop OLP at the same time and vice versa. Those patients who develop skin lesions only are usually free of their LP in approximately 18 months; however, patients with OLP may have their lesions for up to 20 years. Thus, management strategies for the patient with OLP are markedly different than for its skin surface counterpart.

The most common oral presentation of LP is the reticular form. These lesions appear as raised white, linear striations that often interlace in what is termed striae of Wickham. These striations are almost pathognomonic of the disorder. It should be noted that these linear lesions also accompany the erosive form of OLP and occur at the periphery of the eroded area. This is a significant diagnostic clue in the evaluation of the erosive type. The reticular form usually is observed on the buccal mucosa, often bilaterally. Several authors have noted that these lesions are adjacent to gold or silver amalgam restorations in many cases. The lesions are asymptomatic.

The bullous form of OLP is uncommon, perhaps because the oral cavity is a very active region. The functions of chewing, swallowing, and speaking probably do not allow the bulla to remain intact for very long. The size of these lesions is variable, from a few millimeters to several centimeters. The plaque type of OLP appears as a nondescript leukoplakia that needs to be biopsied if no other diagnosis can be made for the lesion. These lesions appear as multiple diffuse, raised white plaques commonly on the buccal mucosa and tongue. Silverman et al have determined that patients with this form of LP tend to be smokers. This may place them at risk for transformation to dysplasia or carcinomatous change.

The atrophic form of OLP can be seen concomitantly with the erosive or reticular forms. This is frequently the type of OLP seen on the gingiva of patients, commonly referred to as desquamative gingivitis. These lesions are symptomatic. The patient may complain of burning and pain while brushing. Because dental plaque has been implicated as a possible antigen, the patient will need to see a dentist for professional maintenance following initial corticosteroid treatment of the lesions.

Erosive LP is the most painful form of OLP. As stated previously, these erosions are seen frequently with the reticular form adjacent to the area. Atrophic or plaque forms may be seen less commonly. Erosive LP may mimic oral cancer, erythema multiforme, lupus erythematosus, and candidiasis. Many drugs can produce lesions that look like erosive LP clinically. (source: D. A. Miles and M. M. Howard, "Disorders affecting the oral cavity: Diagnosis and management of oral lichen planus", Dermatologic Clinics, 1996, 14(2), 281-290.)

Pemphigus

Pemphigus is a rare, autoimmune blistering disease. Of the various forms of pemphigus, pemphigus vulgaris and paraneoplastic pemphigus affect the oral mucosa with regularity. The antigenic targets in pemphigus are components of the desmosome. Binding of autoantibodies to these antigenic proteins, desmogleins and desmoplakins, leads to dissolution of intercellular adhesion with resultant blister formation. Activity of the disease correlates with titers of pemphigus antibody, which can be detected in the serum of patients with the disease by indirect immunofluorescence testing.

Pemphigus was often a fatal disease before the use of systemic corticosteroids. It has a chronic course, and control of the disease becomes more difficult with subsequent flares. The basis of treatment is immunosuppression to decrease antibody synthesis. Relapses may occur when immunosuppressive drugs are tapered. Paraneoplastic pemphigus remains a very difficult disease to treat and continues to have very high mortality rates.

Historically, therapy for pemphigus was initiated with very high doses of prednisone. This initial high dosage proved to have so many adverse effects that in one early study 8% of patients died from complications of treatment (mainly infections) rather than from pemphigus. The authors recommend that pemphigus initially be treated with prednisone, 60 to 80 mg daily, and generally no more than 100 mg daily. Studies have shown that this dosage is usually as effective as higher doses. If there is no response, but the patient remains stable, the authors recommend adding a second immunosuppressive agent rather than increasing the dose of steroids. Although there are no good controlled studies to support this practice, it is also being followed in the treatment of organ transplant rejection to decrease morbidity from corticosteroids. In patients in whom the disease must be rapidly controlled, higher doses of prednisone may be required to stabilize the patient.

Successful treatment of pemphigus has been achieved with prednisone in combination with azathioprine, cyclosporine, cyclophosphamide, dapsone, and gold sodium thiomalate.

Fleischli et al report the successful treatment of pemphigus vulgaris with pulse intravenous cyclophosphamide. Six of nine patients responded to therapy, and two patients achieved remission of skin lesions. One patient was able to discontinue prednisone completely. Two patients died of cardiac complications despite improvement of their skin disease. One patient developed sepsis that was successfully treated with intravenous antibiotics. The investigators concluded that pulse cyclophosphamide may be a useful adjunctive treatment for recalcitrant disease. Long-term side effects such as secondary malignancy may be less likely to result from this treatment than from perorally administered cyclophosphamide because of the lower cumulative doses. Intravenously administered cyclophosphamide should be reserved for patients with severe, recalcitrant disease because of the serious complications that may occur during therapy. (source: J. L. Popovsky and C. Camisa, "New and emerging therapies for diseases of the oral cavity", Dermatologic Clinics, 2000, 18(1), 113-125.)

Radiation Proctitis

Acute complications of pelvic radiation occur with distinct clinical courses and pathologic manifestations. The most frequent serious complication of pelvic radiation is small bowel damage, including thrombocytopenia, leukopenia, dysuria, and effects on the small bowel (diarrhea, abdominal cramping, and increased bowel frequency) and large bowel (acute proctitis, tenesmus, bloody and/or mucus discharge). Sigmoidoscopy during treatment normally reveals an inflamed, edematous, and friable rectal mucosa consistent with acute radiation proctitis. These symptoms are usually transient and resolve within a few weeks following the completion of radiation therapy. They appear to be a function of the dose rate and fraction size rather than the total dose. The mechanism is primarily the depletion of actively dividing cells in what is otherwise a stable cell renewal system. In the small bowel, loss of the mucosal cells results in malabsorption of various substances including fat, carbohydrate, protein, and bile salts. The management of bowel-related complications usually involves the use of diphenoxylate and/or narcotics. The bowel mucosa usually recovers in 1 to 3 months following the completion of radiation. (source: DeVita: Cancer: Principles and Practice of Oncology, 5th ed., Copyright© 1997 Lippincott-Raven Publishers).

Ulcerative Colitis

Inflammatory bowel diseases (IBD), including ulcerative colitis and Crohn's disease, are chronic inflammatory diseases of the gastrointestinal tract. They are diagnosed by a set of clinical, endoscopic, and histologic characteristics, but no single finding is absolutely diagnostic for one disease or the other. Moreover, some patients have a clinical picture that falls between the two diseases and are said to have indeterminate colitis.

The inflammatory response in ulcerative colitis is largely confined to the mucosa and submucosa, but in Crohn's disease the inflammation extends through the intestinal wall from mucosa to serosa. Ulcerative colitis is confined to the colon, and colectomy is a curative procedure. Crohn's disease, in contrast, can involve any part of the gastrointestinal tract, although the distal small bowel and the colon are most commonly involved. Resection of the inflamed segment is not curative in Crohn's disease, and inflammation is likely to recur.

In ulcerative colitis, inflammation begins in the rectum, extends proximally a certain distance, and then abruptly stops, with a clear demarcation between involved and uninvolved mucosa. In mild disease, there are superficial erosions, whereas in more severe disease, ulcers may be large but superficial, penetrating the muscularis mucosa only in very severe disease. Inflammatory polyps or pseudopolyps may be present. Most of the pathologic findings in ulcerative colitis are limited to the mucosa and submucosa; the muscularis propria is affected only in fulminant disease. Active ulcerative colitis is marked by neutrophils in the mucosa and submucosa and clumps of neutrophils in crypt lumens (crypt abscesses). There is mucus depletion, mucosal edema, and vascular congestion with focal hemorrhage. In addition to signs of acute activity, there are also signs of chronicity, with lymphoid aggregates, plasma cells, mast cells, and eosinophils in the lamina propria.

The dominant symptom in ulcerative colitis is diarrhea, which is usually associated with blood in the stool. Bowel movements are frequent but small in volume as a result of irritability of the inflamed rectum. Urgency and fecal incontinence may limit the patient's ability to function in society. Other symptoms include fever and pain, which may be in either lower quadrant or in the rectum. Systemic features— fever, malaise, and weight loss—are more common if all or most of the colon is involved and may have a greater effect than diarrhea on the patient's ability to function. Some patients, especially elderly persons, complain of constipation rather than diarrhea because rectal spasm prevents the passage of stool. The initial attack of ulcerative colitis may be fulminant with bloody diarrhea, but more commonly the disease begins indolently, with non-bloody diarrhea progressing to bloody diarrhea Ulcerative colitis can present initially with any extent of anatomic involvement, from disease confined to the rectum to pancolitis. Most commonly, ulcerative colitis follows a chronic intermittent course with long periods of quiescence interspersed with acute attacks lasting weeks to months; however, a significant percentage of patients suffer a chronic continuous course. (source: Goldman: Cecil Textbook of Medicine, 21st Ed).

In the diseases and disorders listed above, there are either no adequate treatment options, or the treatments, while demonstrating success, may lead to the development of significant adverse side-effects.

It is an aim of the present invention to provide viscous, mucoadhesive liquid formulations to be used for the prevention and treatment of mucocutaneous disorders. The formulation may be used with or without one or more active pharmaceutical agents. These formulations are especially beneficial in diseases and conditions in which a wide area of the mucosal surface requires treatment, but the formulations may also be used in treating small areas of the mucosal surface.

In order that mucocutaneous disorders are treated effectively, it is preferred that the lesion is in contact with the liquid, mucoadhesive formulation for the period of time required to derive benefit. To grant such benefit, this invention describes mucoadhesive, viscous liquid formulations which may or may not contain one or more pharmaceutically active ingredients. The liquid can readily be applied to the affected region of the mucosa by methods known in the art, while the high viscosity and mucoadhesion will cause liquid to remain in contact with the lesion for extended periods. The formulations of the present invention may be applied to treat mucocutaneous lesions in a variety of body compartments, including, but not limited to, the oral cavity, the nasal cavity, the esophagus, the rectum, the bladder, and the vagina.

Furthermore, the viscous, mucoadhesive liquid formulations of the current invention may be used to deliver one or more pharmaceutically active compounds to the mucosal surface, either for the prevention or treatment of diseases and disorders of the mucosa, or for delivery of the pharmaceutically active compound(s) to the systemic circulation by transfer through the mucosa.

SUMMARY OF THE INVENTION

The present invention involves a composition for the treatment and prevention of mucocutaneous disorders. This composition of the present invention, in one embodiment, comprises an amount of a mucoadhesive effective to coat the mucocutaneous area being treated and also a therapeutically or prophylactically active drug for a mucocutaneous disorder. In an important embodiment, the mucoadhesive is at a viscosity-inducing concentration. In another embodiment of the present invention, the mucosal drug delivery composition useable in the treatment or prevention of a mucocutaneous disorder is described. This composition comprises an amount of a mucoadhesive to form an effective coat in the mucocutaneous area being treated, a viscosity-inducing agent and a therapeutic or prophylactic drug for mucocutaneous disorders. The mucoadhesive of the present invention in one embodiment is a linear or cross linked polymer. This polymer will be for example a linear or cross-linked polyacrylic acid, carboxymethylcellulose, hydroxyalkylcellulose, dextran sulfate, dermatan sulfate, a water-soluble vinyl polymer, or chitosan. In the composition of the present invention a mucoadhesive is generally at a concentration between 0.1 w/w % and about 3.0 w/w %. In a preferred embodiment, the mucoadhesive of the present invention is a Carbopol™, (polymer of acrylic acid cross-linked with polyalkenyl ethers or divinyl glycol) most preferably Carbopol 971P™. Useable viscosity-inducing agents are many and include agar, bentonite, glycerin, providone, kaoline, and tragacanth. The composition of the present invention is preferably at a pH between about 6.5 and about 8.5. In an important embodiment of the present invention the composition exhibits pseudoplastic properties as defined elsewhere herein.

Among the mucocutaneous disorders treatable by their methods and compositions of the present invention are: mucositis, Bechet's disease, apthous ulcer, bullous pemphigoid, chemical cystitis, radiation cystitis, erythema multiforme, esophagitis, interstitial cystitis, oral Lichen planus, pemphigus, radiation proctitis, or ulcerative colitis.

An important aspect to the present invention involves a method for the prevention or treatment of mucocutaneous disorders. This method involves identifying a patient having or possibly developing a mucocutaneous disorder. Next in this method is the administration to the patient of a formulation comprising a mucoadhesive agent in an amount effective to prevent or treat the mucocutaneous disorder. Of course, this formulation may and often does include a viscosity-inducing agent and/or a viscosity-enhancing concentration of mucoadhesive. Mucocutaneous disorders treatable by this method are described above. This formulation is often more useful when possessing pseudoplastic behavior, which provides for reduced viscosity during application, allowing the liquid to cover the mucosa more readily, and for increased viscosity of the liquid when in place on a mucocutaneous area. In terms of the length of treatment, this will vary according to the severity and type of disorder. It is expected that the alleviation of mucocutaneous disorders should be visible to anyone treating the patient and that the method of treatment should continue until recovery is clear. This may take from hours to days to weeks, depending upon the situation. Preferred mucoadhesive agents for this method are described above. Likewise, for viscosity-inducing agents.

DETAILED DESCRIPTION OF THE INVENTION

The present invention describes formulations for the prevention and treatment of disorders of mucous membranes in humans and animals. The liquid or other formulations of the present invention are ideally suited to treat diseases and disorders which affect a wide area of the mucosal surface, but they also provide the opportunity to treat discrete, localized lesions, especially in the oral cavity. The mucous membranes which may be treated by the compositions described in this patent include, but are not limited to, those in the oral cavity, the nasal cavity, the gastrointestinal and respiratory tracts, the vagina, and the bladder. Inflammatory, erosive, and/or ulcerative diseases which can be treated by topical application of the compositions described in this patent include, but are not limited to, aphthous ulcers, Behçet syndrome, bullous pemphigoid, chemical or radiation-induced cystitis, erythema multiforme, esophagitis, interstitial cystitis, mucositis, oral lichen planus, pemphigus, and radiation proctitis. In conditions such as aphthous ulcers, chemical or radiation-induced cystitis, mucositis, and radiation proctitis, when the onset of the inflammatory, erosive, and/or ulcerative condition may be forecast (for example, by prodromal sensations in the case of aphthous ulcers, and by initiation of chemotherapy and/or radiation therapy in the treatment of cancer), the compositions of this invention might be applied prior to the formation of lesions, or at the commencement of therapy to prevent or delay the onset of inflammatory, erosive, and/or ulcerative lesions. While a mucoprotective agent may be a mucoadhesive alone, a viscous mucoadhesive solution is preferred particularly when a pharmaceutical agent is present to be selectively transmitted to a mucosal target.

As described later in the examples section, one of the viscous, mucoadhesive solutions of the current invention, a formulation which is composed entirely of pharmaceutically-accepted excipients, demonstrated a surprising result in a clinical study. This study examined the degree of mucositis in patients receiving radiotherapy for head and neck cancer. The mean and median mucositis scores for patients rinsing six times a day with one of the viscous, mucoadhesive solutions of the current invention for the duration of radiation therapy (6-7 weeks), with or without concombinant chemotherapy, were much lower than the scores for patients who did not use this rinse.

There is currently no complete explanation of why the viscous, mucoadhesive solutions of the current invention without a known active pharmaceutical ingredient should provide such benefit to patients. The following are considered viable possibilities, but this invention should not be considered as limited to any one of these possibilities A viscous, mucoadhesive solutions provides a layer on the surface of the mucosa for an extended period, and this may have a beneficial effect, for example, a moisturizing or barrier effect, so limiting the damage to the mucosal surface caused by disease, or injury from ionizing radiation and/or chemotherapeutic agents. Thus, it is envisioned that any aqueous solution which is formulated with non-toxic and non-irritating excipients and providing a solution which is both viscous and mucoadhesive might be expected to provide benefit to patients suffering a disease or disorder of the mucosa.

It is known that polyanionic carbohydrate polymers and oligomers can have a beneficial effect in the treatment of mucosal disorders. For example, pentosan polysulfate and hyaluronic acid are known to provide benefit to patients with interstital cystitis (Morales A, et al, Treatment of refractory interstitial cystitis, Int Urogynecol J Pelvic Floor Dysfunct 1996; 7(4):215-20). It is quite possible that other polyanionic and polycationic compounds, whether carbohydrate, of natural origin or synthetic, may also provide benefit in the prevention and treatment of mucosal disorders. Linear and partially cross-linked polyanionic polymers are included in the formulation used in the product demonstrating benefit in the mucositis clinical study described in the examples.

Other components of the formulation used in the clinical study, benzyl alcohol, citric acid, glycerin, polysorbate 60, and saccharin, alone or in combination with each other and/or the other excipients of the formulation may have a beneficial effect. Other preservatives, humectants, emulsifying agents, antioxidants, antimicrobial agents, solubilizing agents, and other excipients known in the art in the formulation of liquid pharmaceutical products, alone or in combination, may also provide for, or enhance, the beneficial properties on mucosal surfaces, when formulated to provide a viscous, mucoadhesive solution.

Viscous, mucoadhesive formulations for the prevention and treatment of mucosal diseases and disorders may additionally be formulated with one or more compounds known to be pharmaceutically active. Addition of further pharmaceutically active compounds could provide greater benefit to patients in the prevention and treatment of mucosal disorders. Examples of pharmaceutically active compounds which could be incorporated in the viscous, mucoadhesive solutions of this invention as provided later in this section.

Aqueous solutions of pharmaceutically-active compounds are well known in the art as convenient drug delivery formulations. Such formulations are most useful for oral delivery, when the solution is swallowed, and the drug is presented to the stomach and gastrointestinal tract in a form which is amenable to rapid absorption. Aqueous solutions are also used to deliver drugs to mucosal tissue. In general, aqueous solutions used to deliver pharmaceuticals tend to be non-viscous and non-mucoadhesive. For oral delivery, this property is undesirable, as it minimizes the amount of drug which is retained in the oral cavity and esophagus, while maxim g that delivered to the stomach and gastrointestinal tract. One preferred drug for the treatment of mucocutaneous disorders is amlexanox.

For topical treatment of mucosal membranes, aqueous solutions of pharmaceutically-active compounds offer the advantage over other dosage forms in that a wide area of the mucosa can be readily covered with the solution, which is of benefit if the area to be treated is not a single, discrete region. Also, mucosa not readily accessible can be treated using aqueous solutions of pharmaceutically-active compounds and simple methods of application. However, formulations which are non-mucoadhesive and non-viscous are less than ideal for delivery of drugs to mucosal surfaces. Such solutions will be rapidly removed from the area being treated, for example, because the liquid flows from the site of application under the influence of gravity, and/or because the natural secretions of mucosal membranes carry the solution from the site of application.

The present invention involves a finding that neither high viscosity nor mucoadhesion alone confers ideal properties. A viscous but non-mucoadhesive liquid will not be held in place on the mucosal surface. Instead, a non-mucoadhesive solution will readily be lost from the point of application, for example, under the influence of gravity, and/or through natural movements of the membrane and surrounding structures, and/or the flow of natural secretions. In an aqueous liquid formulation which is mucoadhesive but has low viscosity, only a thin layer of the liquid which is adjacent to the mucosa may be held in place, but the bulk of the liquid might rapidly flow from the site of application under the influence of gravity and/or be readily removed by the natural secretions of mucosal membranes. In a mucoadhesive, viscous liquid formulation, the liquid will adhere to the mucosa, while the high viscosity of the liquid will reduce the rate of removal of the bulk of the liquid from the site of application. In some cases a low viscosity mucoadhesive may provide effective treatment, especially when pharmaceutical agents are not required. A mucoadhesive agent may itself be a viscosity-inducer and thus serve two purposes. The term "viscosity-inducing" is meant to mean enhancement of the aqueous mucoadhesive layer that adheres to mucosal areas.

Mucoadhesive formulations are well known in the art. However, known formulations intended for extended drug delivery to (or close to) the site of application of a mucoadhesive formulation are either solids or semi-solids. Examples of the former include tablets, powders, lozenges, and films. Examples of mucoadhesive semi-solids include gels, pastes, ointments, and creams. Few, if any, examples are known in which a mucoadhesive viscous liquid is used as a drug delivery system.

For most liquids, viscosity remains constant over a wide range of shear rates. This phenomenon is known as Newtonian viscosity, and liquids which display this property are called Newtonian liquids. Liquids in which viscosity varies with shear rate are termed non-Newtonian. There are several known non-Newtonian profiles. One of these profiles is termed pseudoplastic, and liquids which fall into this category demonstrate a decrease in viscosity as shear rate increases. Preferred formulations of the current invention are pseudoplastic, and demonstrate a decrease in viscosity at low shear rates. Pseudoplasticity benefits the application of the formulations of the current invention by virtue of the fact that application of shear (for example, swishing the liquid in the mouth) reduces the viscosity, so allowing the liquid to flow and coat the mucoscal surface more readily. Once the shear forces are discontinued, the viscosity of the liquid increases, as required (in combination with mucoadhesion) for prolonged attachment to the mucosal surface.

Formulations of the current invention are viscous, free-flowing liquids (i.e., not gels) that are either Newtonian or pseudoplastic. The ability to flow freely is desired in order to readily coat either a selected region or a wide area of the affected mucosal membrane, and to coat mucosal membranes not readily accessible to simple application. The solutions of the current invention will have viscosities at zero shear in the range 100-20,000 cP.

The stable, viscous, mucoadhesive liquid formulations of the present invention may be applied to mucosal membranes for the delivery of pharmaceutically active compounds to the mucosal membranes for prevention and/or treatment of disorders or diseases of these membranes, or for the delivery of pharmaceutically active compounds to systemic circulation by passage through the mucosal membrane. The liquid may be applied, e.g., to the following mucosal surfaces; the oral cavity, the nasal cavity, the gastrointestinal and respiratory tracts, the vagina, and/or the bladder. The formulations of the current invention may also be applied to other mucous membranes for the prevention and treatment of disorders and diseases. Many methods known in the art for the delivery of liquids to body compartments may be used.

For treatment of disorders and diseases of the oral cavity, the preferred stable, viscous, mucoadhesive liquid formulations of the current invention may be taken by mouth and distributed throughout the oral cavity by a swishing action, or by the patient adopting a slow circulating movement of the head. Excess solution can either be swallowed or expelled.

For treatment of disorders and diseases of the esophagus, the stable, viscous, mucoadhesive liquid formulations of the current invention can be swallowed with minimal contact of the oral cavity, or administered by gavage, or by spraying the liquid into the throat.

For treatment of disorders and diseases of the nasal cavity, the stable, viscous, mucoadhesive liquid formulations of the current invention can be delivered as droplets or by spraying the liquid into the nose.

For treatment of disorders and diseases of the bladder, the stable, viscous, mucoadhesive liquid formulations of the current invention can be delivered by intravesical administration.

For treatment of disorders and diseases of the rectum and lower gastrointestinal tract, the stable, viscous, mucoadhesive liquid formulations of the current invention can be administered by catheter or enema.

Other methods to apply the stable, viscous, mucoadhesive liquid formulations of the current invention to mucosal tissues are known to those skilled in the art.

Pharmaceutically active compounds which may be formulated with the viscous, mucoadhesive liquid formulations of the current invention, either for topical treatment of a mucosa, or for transfer of the pharmaceutically active ingredient to the systemic circulation can include, either alone or in combination, one or more of the following classes of drugs: anti-allergy compounds, anti-inflammatory analgesic agents, steroidal and non-steroidal anti-inflammatory agents, anabolic steroids, analgesics, antihistamines, local anesthetics, bactericides and disinfectants, vasoconstrictors, hemostatics, chemotherapeutic agents, antibiotics, keratolytics, cauterizing agents, and antiviral drugs. Other classes of pharmaceutically active agents may also be formulated with the viscous, mucoadhesive liquid formulations of the current invention.

Examples of anti-inflammatory analgesic agents include acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, etc.

Examples of steroidal anti-inflammatory agents include hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, etc.

Examples of anabolic steroids include testosterone and oxandrolone.

Examples of antihistamines include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, etc.

Examples of local anesthetics include dibucaine hydrochloride, dibucaine, lidocaine hydrochloride, lidocaine, benzocaine, p-buthylaminobenzoic acid 2-(die-ethylamino)ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, etc.

Examples of bactericides and disinfectants include thimerosal, phenol, thymol, benzalkonium chloride, benzethonium chloride, chlorhexidine, povidone iodide, cetylpyridinium chloride, eugenol, trimethylammonium bromide, etc.

Examples of vasoconstrictors include naphazoline nitrate, tetrahydrazoline hydrochloride, oxymetazoline hydrochloride, phenylephrine hydrochloride, tramazoline hydrochloride, etc.

Examples of hemostatics include thrombin, phytonadione, protamine sulfate, aminocaproic acid, tranexamic acid, carbazochrome, carbaxochrome sodium sulfanate, rutin, hesperidin, etc.

Examples of chemotherapeutic drugs include sulfamine, sulfathiazole, sulfadiazine, homosulfamine, sulfisoxazole, sulfisomidine, sulfamethizole, nitrofurazone, taxanes, platinum compounds, topoisomerase I inhibitors, and anthracycline.

Examples of antibiotics include penicillin, meticillin, oxacillin, cefalotin, cefalordin, erythromeycin, lincomycin, tetracycline, chlortetracycline, oxytetracycline, metacycline, chloramphenicol, kanamycin, streptomycin, gentamicin, bacitracin, cycloserine, and clindamycin.

Examples of keratolytics include salicylic acid, podophyllum resin, podolifox, and cantharidin. Examples of cauterizing agents include the chloroacetic acids and silver nitrate.

Examples of antiviral drugs include protease inhibitors, thymadine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Examples of anti-allergy compounds include alopatadine, astemizole, cromolyn, fenpiprane, repirinast, tranilast, traxanox, etc.

The amount of pharmaceutically active compound(s) to be used depends on the desired treatment strength, although preferably, the pharmaceutical component comprises 0.001 to 30% by weight of the formulation, and more preferably between 0.005 and 20% by weight.

In addition to the preferred requirements of mucoadhesion and viscosity as described above, it is important, for use of the formulation for the prevention and treatment of mucosal diseases and disorders, and for use of the formulation as a drug delivery vehicle that the liquid solution be stable, such that it can be stored at ambient temperatures for many months or years, even when subjected to brief periods of elevated or depressed temperatures, without physical or chemical degradation of the formulation. It is usually desirable to formulate the product without use of any organic solvents, the presence of which might irritate the mucosal lesions being treated. Furthermore, it is desirable to formulate the viscous, mucoadhesive solution using only excipients which are accepted by all major pharmaceutical regulating authorities as safe.

The following list provides examples of components of the stable, viscous, mucoadhesive formulations of the current invention:

A linear or cross-linked polymer polyanionic or polycationic polymer which may or may not already be known to provide mucoadhesion. Such polymers include (but are not limited to) polyacrylic acid, a cross-linked homopolymer based on acrylic acid, a crosslinked copolymer based on acrylic acid, carboxymethylcellulose, hydroxyalkylcellulose, dextran sulfate, dermatan sulfate, and hyaluronic acid. Other mucoadhesive polymers are well-known to those skilled in the art. The viscous, mucoadhesive formulations of the current invention can contain a single mucoadhesive component, or mixtures thereof. The preferred mucoadhesive polymers are cross-linked homopolymers and copolymers based on acrylic acid, especially the Carbopol and Noveon polymers supplied by B.F. Goodrich; most preferred is Carbopol 971P.

Viscosity enhancement is provided by one or more of the above mentioned mucoadhesive polymers alone or in combination with agar, bentonite, glycerin, povidone, kaolin, and/or tragacanth. Most preferred is Carbopol 971P in combination with glycerin.

The pH of the solution is adjusted to the final desired pH with any pharmaceutically accepted acid or base. Most preferred are sodium or potassium hydroxide, phosphoric acid, or citric acid. A final pH of 6.5 to 8.5 is preferred.

To prevent microbial growth in the formulation during storage, it is desirable to include a preservatives. Preservatives known in the art include benzyl alcohol, benzoate salts, phenoxyethanol, methylparaben, and propylparaben. Benzyl alcohol is the most preferred preservative.

A humectant is desirable to provide a pleasant mouth-feel in oral applications. Humectants known in the art include cholesterol, fatty acids, glycerin, lauric Acid, magnesium stearate, pentaerythritol, and propylene glycol. Glycerin is preferred.

An emulsifying agent might be necessary, for example to ensure complete dissolution of all excipients, especially hydrophobic components such as benzyl alcohol. Many emulsifiers are known in the art. The preferred emulsifier is polysorbate 60.

For oral applications, it may be desirable to add a pharmaceutically acceptable flavoring agent and/or sweetener. Compounds such as saccharin, glycerin, simple syrup, and sorbitol are useful among those as sweeteners. Saccharin is preferred.

It may be desirable to include other ingredients; for example a pharmaceutically acceptable organic solvent, a buffering agent, an antioxidant, an antimicrobial agent, and/or a coloring agent. The exact formulation of the above ingredients, and the method of manufacture, will be apparent to those skilled in the art. A number of texts provide assistance in the design and manufacture of pharmaceutical formulations, including Remington's Pharmaceutical Sciences, Mack Publishing Company Co., Easton, Pa., and Pharmaceutical dosage forms and drug delivery, Ansel et al, 1995, Williams and Wilkins, Malvern, Pa.

Figure 1:
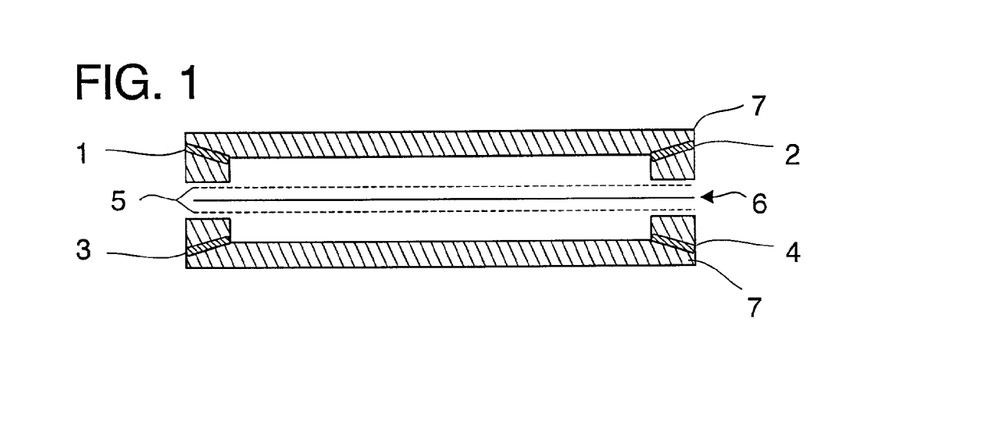
FIGS. 1 and 1a show an in vitro model developed to demonstrate the enhanced delivery of active pharmaceutical ingredients to the surface of mucosal membranes.
Figure 1A:
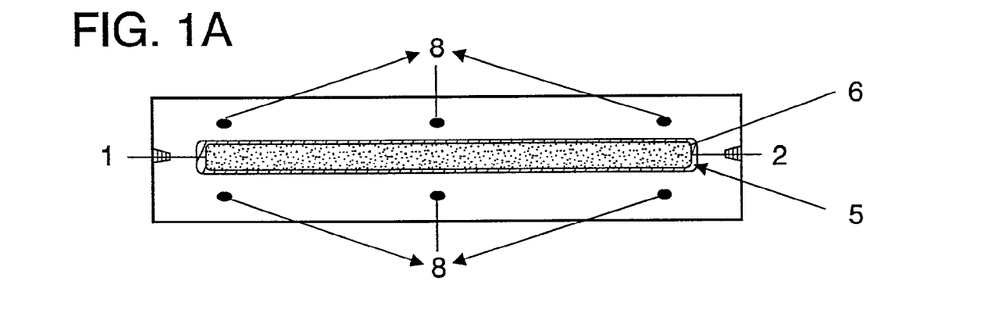

An in vitro model was developed to demonstrate the enhanced delivery of active pharmaceutical ingredients to the surface of mucosal membranes. In the following example, amlexanox was used as the test compound. Referring to FIG. 1 and FIG. 1a, there are two identical clear polycarbonate blocks 7 which are 1.2 cm×4.7 cm×11.5 cm having a 0.2 cm×1.0 cm×10.1 cm flat-bottomed groove. Each opposing end of the flat-bottomed groove has a $^{10}/_{32}$" port 1-4 for connecting tubing for the flow of artificial saliva and/or adding sample solutions. Separating the two identical clear polycarbonate blocks 7 is a Spectra/Por 4 dialysis membrane 6 which has a layer of Gore-Tex® GR gasket sheeting 6 on both sides to prevent leakage. The two identical halves of polycarbonate 7 are joined together to form a watertight flow cell with six bolts and six wing nuts 8.

EXAMPLES

Example 1

Preparation of Viscous, Mucoadhesive Aqueous Composition

A viscous, mucoadhesive aqueous solution was formulated by adding Carbopol® 971P NF to water using an appropriate mixing apparatus (Master Servodyne® mixer with high-lift blade rotating at 200-300 rpm) to give a clear solution. An aqueous solution of potassium hydroxide was added with stirring to give a clear gel. An aqueous solution of potassium hydroxide, citric acid, saccharin sodium, phosphoric acid and glycerin was added with stirring to give a clear solution. A solution of benzyl alcohol and polysorbate 60 was added with stirring to give a clear solution. The pH was adjusted to 7.0-7.8 with an aqueous solution of phosphoric acid. The resulting product was mixed further for 30 minutes.

The formulation of the product is set out, below in Table 1:

TABLE 1

| Ingredients | Weight Percent |
|---|---|
| purified water | 90.68 |
| 10% potassium hydroxide | c.a. 4.6 |
| benzyl alcohol | 1.50 |
| polysorbate 60 | 0.05 |
| Carbopol ® 971P | 0.35 |
| 0.5% phosphoric acid | c.a. 5.7 |
| citric acid | 0.05 |
| saccharin sodium | 0.40 |
| glycerin | 5.00 |
| Natural Orange Flavor | 0.05 |

Example 2

Preparation of Viscous, Mucoadhesive Aqueous Composition Containing Amlexanox

The method set out in Example 1 was followed to provide a viscous, mucoadhesive aqueous composition of the following formula shown in Table 2:

TABLE 2

| Ingredients | Weight Percent |
|---|---|
| purified water | 91.21 |
| potassium hydroxide | 0.60 |
| benzyl alcohol | 1.50 |
| polysorbate 60 | 0.05 |
| Carbopol ® 971P | 0.35 |
| phosphoric acid | 0.13 |
| citric acid | 0.05 |
| saccharin sodium | 0.40 |
| amlexanox | 0.50 |
| Glycerin | 5.20 |

Example 3

High Performance Liquid Chromatographic Assay for the Amlexanox

The following HPLC parameters were employed in performing an assaying for amlexanox:
Phenomenex, Prodigy, 5 Φm ODS (2), 150 mm×4.6 mm
Mobile Phase: 25% THF/75% 10 mM phosphate buffer, pH 8.0
Flow Rate: 1.0 mL/min
Injection Volume: 10 ΦL
Detector: UV@244 nm

Example 4

Figure 2:
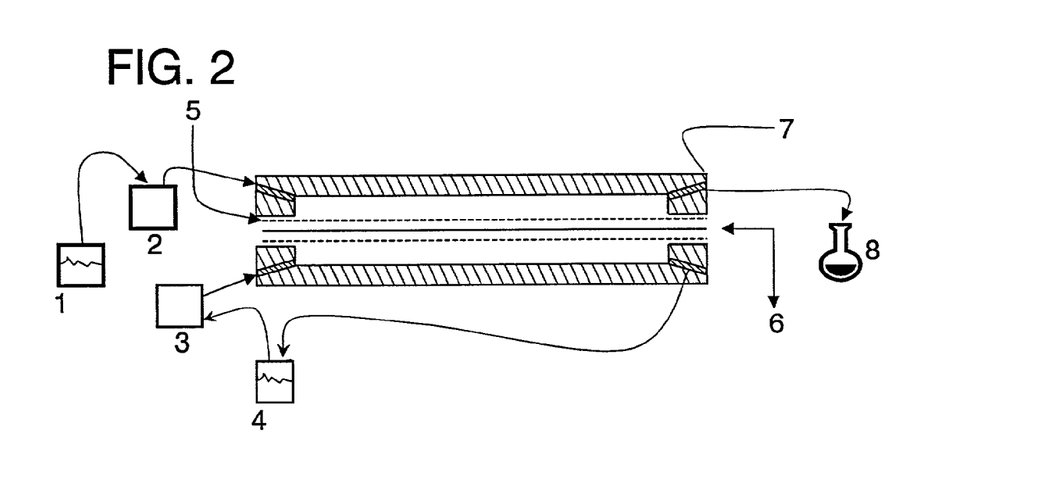
FIG. 2 shows the device described in FIG. 1 is attached to LC pumps 2-3 using 10/31" ferules and large diameter HPLC tubing.

Demonstration of Drug Delivery from Liquid Formulations in an in Vitro Model of a Mucosal Surface Referring to FIG. 2, the device described in FIG. 1 is attached to LC pumps 2-3 using $^{10}/_{32}$" ferules and large diameter HPLC tubing. One half of the polycarbonate block 7 has a reservoir 1 that provides a continuous flow artificial saliva across the Spectra/Por4 dialysis membrane 6 and is eluted into a 10 mL vessel 8. The opposing half of the polycarbonate block 7 is connected to a LC pump 3 which has a reservoir 4 of artificial saliva that constantly recirculates across the dialysis membrane 6.

In separate experiments, the composition of example 1 was compared with two aqueous formulations of amlexanox which were mucoadhesive but non-viscous, and viscous but non-mucoadhesive, to demonstrate that both properties are required for optimal drug delivery from a free-flowing liquid formulation.

2.9-3.1 mL of the aqueous formulation of amlexanox is applied to the dialysis membrane of the in vitro system, and the flow of artifical saliva was initiated at a rate of 1.0 mL/min. mL samples were withdrawn from the reservoirs 4 and 6 and samples were assayed for amlexanox content using the HPLC assay described in Example 3.

Figure 3:
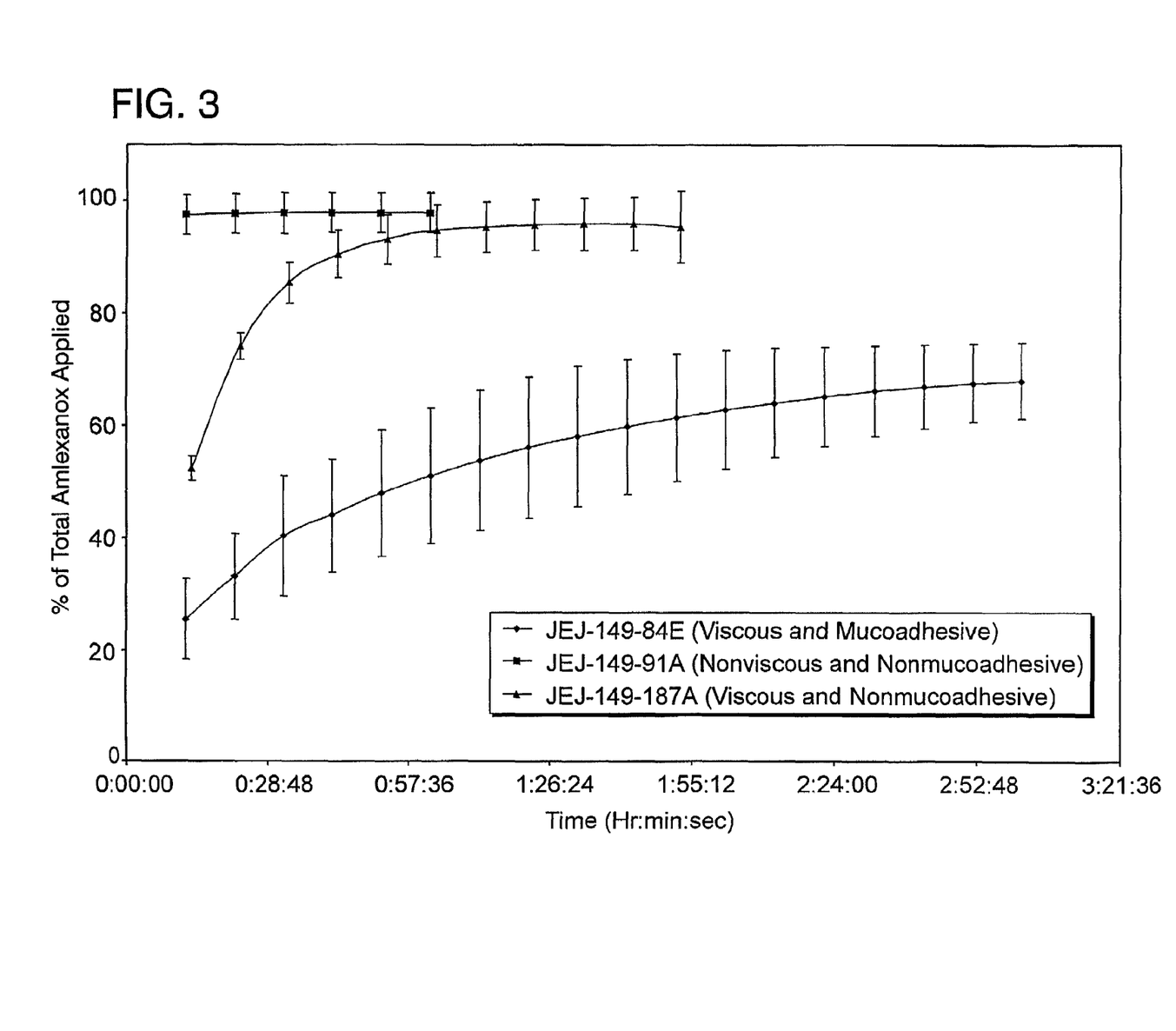
FIGS. 3 and 4 show results of amlexanox delivery of three different formulations when tested using the device shown in FIGS. 1 and 2.
Figure 4:
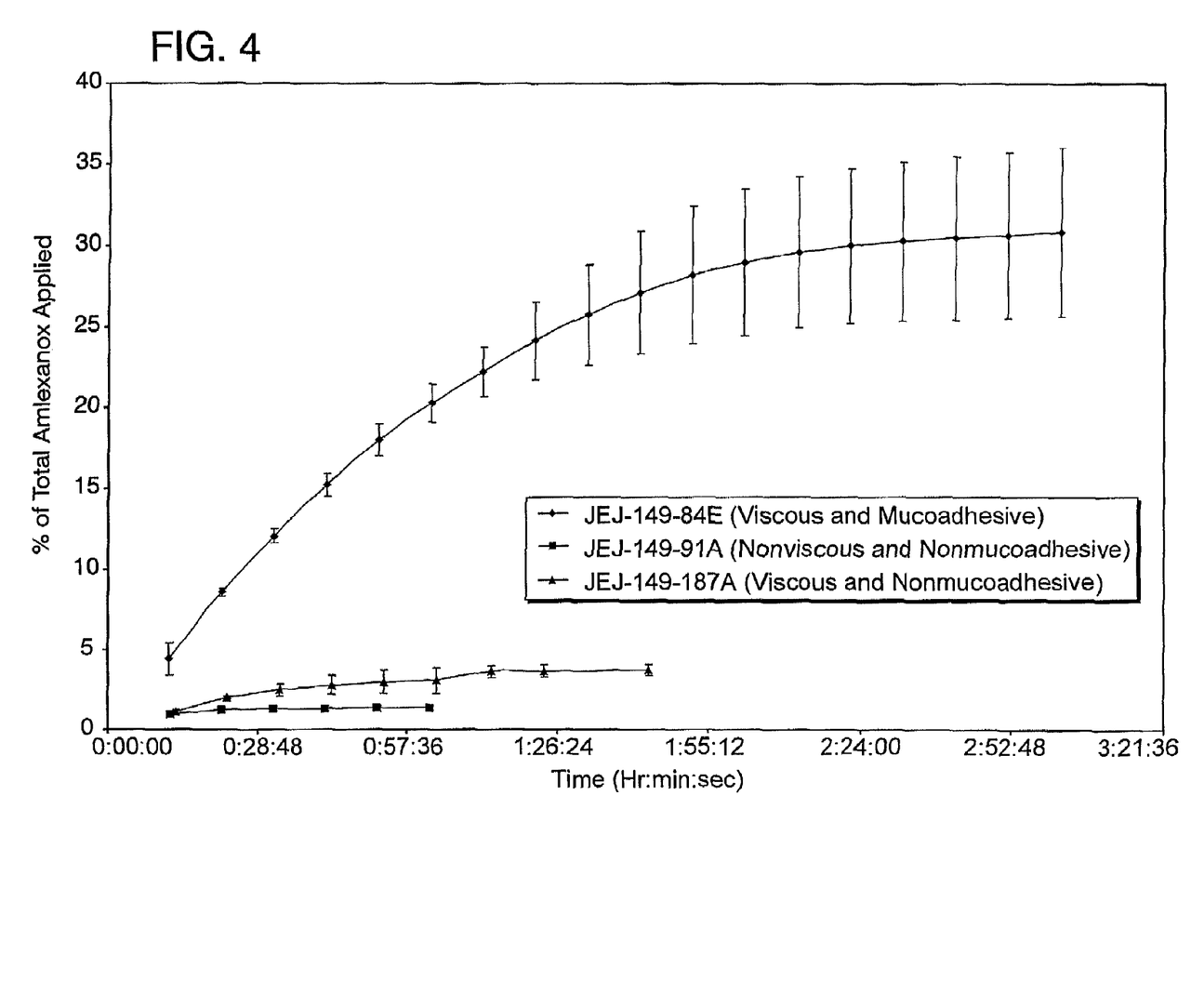

The results of this study are shown in FIGS. 3 and 4. As can be seen in FIG. 3, much less amlexanox is washed away in the simulation of saliva flow in the case of the viscous, mucoadhesive solution which is the subject of this invention compared with the other two formulations. As a result, much more amlexanox (the data indicates a ten-fold difference) is delivered to the membrane and transported to the receiver vessel in the case of the viscous, mucoadhesive solution which is the subject of this invention compared with the other two formulations (shown in FIG. 4).

Example 5

Stability Study

The composition of example 2 was subjected to a stability study. The clear solution was packaged in clear glass bottles which were sealed with white screw caps fitted with teflon liners. The bottles were divided into two groups. One group was stored in a stabilty chamber set at 25° C./60% relative humidity, while the second group was stored at 40° C./75% relative humidity. Bottles were examined at 0, 1, 2, 3, and 6 months for physical appearance (clarity of the solution), package integrity, amlexanox and benzyl alcohol contents, pH, and viscosity. At all times and under both conditions, no physical or chemical changes were noted.

Example 6

Rheology Study

Figure 5:
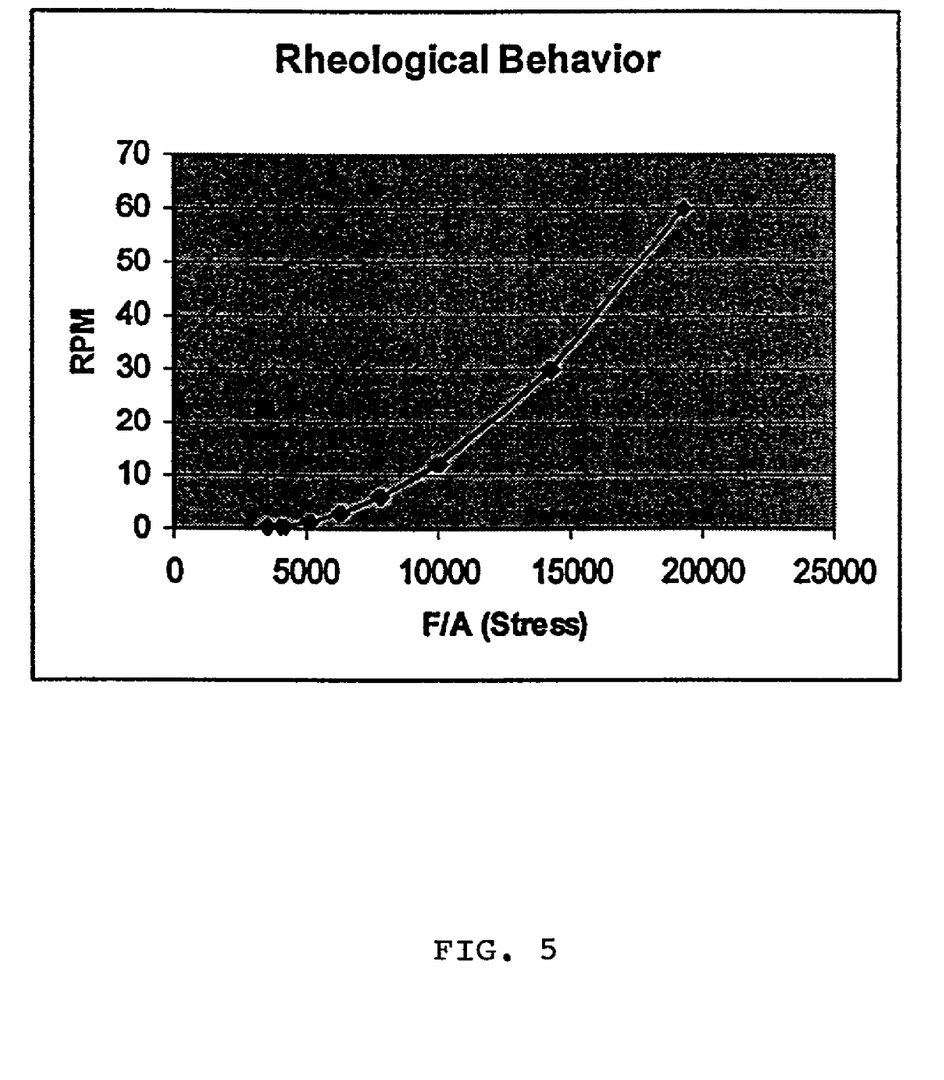
FIG. 5 shows the Theological behavior of the formulation.

A Brookfield viscometer was used to determine the rheological behavior of the oral rinse at 37±1° C. A rheogram was generated by progressively increasing RPM, from 0.3 up to 60 RPM (upcurve) recording the % Torque after each reading stabilized. The upcurve was immediately followed by a downcurve, from 60 RPM to 0.3 RPM. Viscosity is calculated at each RPM, and the stress is then determined by multiplying the viscosity by the RPM. The rheological profile was generated by plotting stress (e.g., F/A) on the x-axis and RPM (e.g., Rate of Shear) on the y-axis, and this result is presented in the FIG. 5.

The rinse is clearly pseudoplastic, yet it does not present any hysteresis. This shear-thinning system has an apparent viscosity that exceeds 10,000 cP at the lowest rate of shear, but that falls to approximately 322 cP at 60 RPM, the highest rate of shear employed.

Example 7

Clinical Study

A clinical study was conducted in patients 18 years of age or older with a histologically documented diagnosis of head-and-neck cancer and a KPS of at least 60%, who received a radiation dose of at least 60 Gy over 6-7 weeks with radiation fields to include at least 40% of the oral mucosa. Patients receiving concomitant chemotherapy were also included in the study. The patients rinsed using the solution exemplified in example 1 for 6 times a day (5 mL each time) for the duration of the radiation treatment (6-7 weeks), beginning on the first day of radiation therapy. An objective measurement of the degree of mucositis (the "Sonis Scale", described in Cancer, 1999, 85(10) 2103-13) was made three times a week for the duration of the study. Table 3 demonstrates the mean and median scores of patients on days 14, 28, and 39. These data were obtained on 12 subjects. Historical data (Sonis scale mucositis scores for a similar patient population, 17 patients in total, undergoing similar treatment for head-and-neck cancer) are provided for comparison.

TABLE 3

| | Median | | |
|---|---|---|---|
| | Day 14 | Day 28 | Day 39 |
| No Treatment | 0.88 | 1.50 | 1.70 |
| Rinse (example 1) | 0.87 | 0.44 | 0.39 |
| | Mean | | |
| | Day 14 | Day 28 | Day 39 |
| No Treatment | 1.01 | 1.50 | 1.62 |
| Rinse (example 1) | 0.44 | 0.81 | 0.85 |

These results clearly show the mucoprotective effects.

Figure 6:
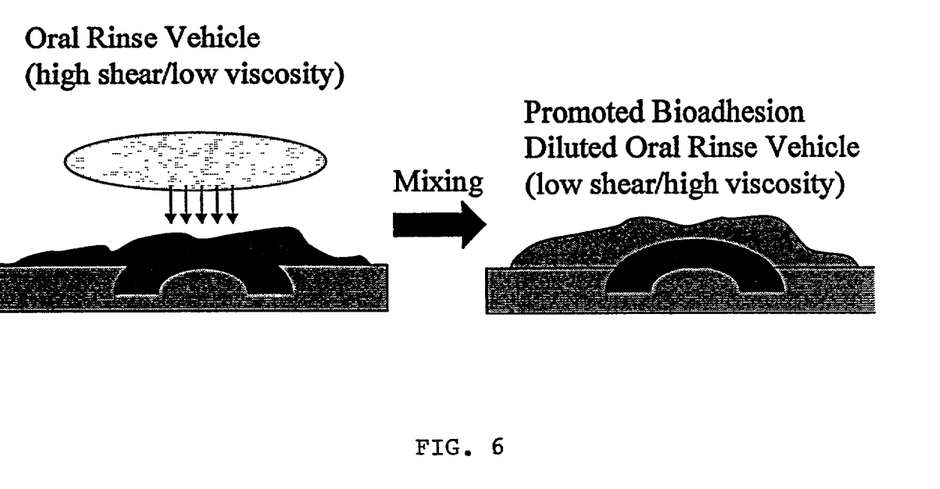
FIG. 6 shows the benefit of a pseudoplastic liquid.

One conclusion here is that the oral rinse vehicle promotes healing of sores in the oral cavity because of the deposition of a bioadhesive polymer (i.e., Carbopol 971P), and the resulting protective action. The sequence of steps associated with this process and some important product attributes are represented in FIG. 6.

When the pseudoplastic, shear-thinning vehicle is mechanically circulated within the oral cavity during the rinsing process, the viscosity is lowered. This permits effective distribution of the liquid, and because it is aqueous in nature with a high surface energy, it readily mixes with endogenous fluid at the tissue surface. To the extent that a polymer-substrate interaction is important for healing, the low viscosity permits diffusion of the bioadhesive polymer to the tissue surface. When mechanical agitation ceases, there is a rapid viscosity increase, essentially creating a protective gel. This gel provides physical protection from direct contact with irritants. Also, Carbolpol 971P has a microviscosity essentially equal to its macroviscosity, and that precludes diffusion or movement of small molecules or microorganisms through the gel to the tissue surface.

For the rinse vehicle system to be most effective, the following the system needs to possess the following attributes:
Pseudoplastic, non-thixotropic behavior
Appropriate initial viscosity of rinse under agitation conditions in the mouth
Appropriate diluted viscosity under agitation conditions in the mouth
Appropriate diluted viscosity without agitation in the mouth
Also, the resulting gel structure may be important or the current product is indeed effective at promoting healing, it has a favorable, and perhaps unique set of these attributes.

What is claimed is:

1. A pseudoplastic liquid composition for treating or inhibiting an oral mucocutaneous disorder, said liquid composition having a zero shear viscosity at 37±1 degrees Celsius of 100-20,000 centipoise, comprising 0.1 to 3.0 wt/wt % of one or more mucoadhesives in an aqueous solution, wherein the mucoadhesive(s) is/are one or more linear or cross-linked polymer(s) selected from the group consisting of polyacrylic acid, carbopol, carboxymethylcellulose, hydroxyalkylcellulose, dextran sulfate, chitosan, and a water-soluble vinyl polymer; wherein said liquid composition, when administered to an oral mucosa:
   1) remains liquid when shear is applied due to swishing the liquid in the mouth; and
   2) attaches to and coats the oral mucosa upon discontinuance of said shear.

2. The pseudoplastic liquid composition of claim 1, further comprising a drug that is therapeutically active against the oral mucocutaneous disorder.

3. The pseudoplastic liquid composition of claim 1, wherein the mucoadhesive is carbopol.

4. The pseudoplastic liquid composition of either of claim 1 or claim 2, further comprising one or more viscosity-inducing agent(s).

5. The pseudoplastic liquid composition of either of claim 1 or claim 2, wherein the mucocutaneous disorder is mucositis, Bechet's disease, apthous ulcer, bullous pemphigoid, chemical systitis, radiation cystitis, erythema multiforme, esophagitis, interstitial cystitis, oral Lichen planus, pemphigus, radiation proctitis, or ulcerative colitis.

6. A pseudoplastic liquid composition for treating or inhibiting an oral mucocutaneous disorder, said liquid composition having a zero shear viscosity at 37±1 degrees Celsius of 100-20,000 centipoise, comprising 0.35 w/w % of one or more mucoadhesives in an aqueous solution, wherein the mucoadhesive(s) is/are one or more linear or cross-linked polymer(s) selected from the group consisting of polyacrylic acid, carbopol, carboxymethylcellulose, hydroxyalkylcellulose, dextran sulfate, chitosan, and a water-soluble vinyl polymer; wherein said liquid composition, when administered to an oral mucosa:
   1) remains liquid when shear is applied due to swishing the liquid in the mouth; and
   2) attaches to and coats the oral mucosa upon discontinuance of said shear.

7. A pseudoplastic liquid composition for treating or inhibiting an oral mucocutaneous disorder, said liquid composition having a zero shear viscosity at 37±1 degrees Celsius of 100-20,000 centipoise, comprising 0.35 w/w % of one or more mucoadhesives and 5 w/w % of a viscosity inducing agent in an aqueous solution; wherein said liquid composition, when administered to an oral mucosa:
   1) remains liquid when shear is applied due to swishing the liquid in the mouth; and
   2) attaches to and coats the oral mucosa upon discontinuance of said shear.

8. The pseudoplastic liquid composition of either of claim 6 or claim 7, further comprising a drug that is therapeutically active against the oral mucocutaneous disorder.

9. The pseudoplastic liquid composition of either claim 6 or 7, wherein the one or more mucoadhesive is carbopol.

10. The pseudoplastic liquid composition of claim 7, wherein the viscosity inducing agent is glycerin.

11. A pseudoplastic liquid composition for treating or inhibiting an oral mucocutaneous disorder, said liquid composition having a zero shear viscosity at 37±1 degrees Celsius of 100-20,000 centipoise, comprising 0.35 w/w % of cabopol, 1.5 w/w % of benzyl alcohol, 0.4 w/w % of sodium saccharin, and 0.05% w/w % of polysorbate 60 in an aqueous solution; wherein said liquid composition, when administered to an oral mucosa:
   1) remains liquid when shear is applied due to swishing the liquid in the mouth; and
   2) attaches to and coats the oral mucosa upon discontinuance of said shear.

12. The pseudoplastic liquid composition of claim 11, further comprising a drug that is therapeutically active against the mucocutaneous disorder.

13. The pseudoplastic liquid composition of claim 11, wherein the composition further comprises one or more viscosity-inducing agent (s).

14. The pseudoplastic liquid composition of any of claims 1, 2, 3, 6, 7, and 10-13, wherein said pseudoplastic liquid composition has a zero shear viscosity at 37±1 degree Celsius of 5,000-20,000 centipoise.

15. The pseudoplastic liquid composition of claim 4, wherein said pseudoplastic liquid composition has a zero shear viscosity at 37±1 degree Celsius of 5,000-20,0000 centipoise.

16. The pseudoplastic liquid composition of claim 5, wherein said pseudoplastic liquid composition has a zero shear viscosity at 37±1 degree Celsius of 5,000-20,0000 centipoise.

17. The pseudoplastic liquid composition of claim 8, wherein said pseudoplastic liquid composition has a zero shear viscosity at 37±1 degree Celsius of 5,000-20,0000 centipoise.

18. The pseudoplastic liquid composition of claim 9, wherein said pseudoplastic liquid composition has a zero shear viscosity at 37±1 degree Celsius of 5,000-20,0000 centipoise.

* * * * *